United States Patent [19]

Takemura et al.

[11] 4,108,912
[45] Aug. 22, 1978

[54] TWO-STAGE HYDROGENATION OF BENZENE TO FORM CYCLOHEXANE USING NICKEL CATALYST

[75] Inventors: Toshisade Takemura; Shohzaburo Sugi; Kenji Nagata, all of Tokuyamashi; Ryohhei Yahagi, Ichiharashi, all of Japan

[73] Assignee: Idemitsu Petrochemical Co., Ltd., Tokyo, Japan

[21] Appl. No.: 797,964

[22] Filed: May 18, 1977

[30] Foreign Application Priority Data

May 19, 1976 [JP] Japan ................................ 51-56709

[51] Int. Cl.$^2$ .............................................. C07C 5/10
[52] U.S. Cl. .................................................... 260/667
[58] Field of Search ..................... 260/667; 208/57, 89

[56] References Cited

U.S. PATENT DOCUMENTS 3,304,338  2/1967  Parish ................................... 260/667
3,679,574  7/1972  Irvine .................................... 208/89

Primary Examiner—Veronica O'Keefe
Attorney, Agent, or Firm—Fred Philpitt

[57] ABSTRACT

In a process for carrying out a reaction in a plurality of catalyst zones arranged in series which shows remarkable rise of reaction temperature due to its high initial activity, an improvement is provided by starting the reaction with a first reactor in which its catalyst activity is reduced in advance so as to make it easier to control the reaction temperature; with other reactors in which their catalyst activities are maintained at higher values with an increasing gradient and with a last reactor in which its catalyst activity is made sufficiently larger in order to be able to maintain the initial value of total conversion with all the reactors even at a time when the catalyst activity of the first reactor is reduced to unusable extent, interrupting the reaction when the catalyst activity of the first reactor is reduced to unusable extent, transferring the first reactor to the next to the last reactor after charged with a new catalyst, and repeating the operation in the subsequent run as in the first run except that the order of each of the reactors is advanced by one in each time of the transfer of the first reactor to the last.

1 Claim, No Drawings

TWO-STAGE HYDROGENATION OF BENZENE TO FORM CYCLOHEXANE USING NICKEL CATALYST

DESCRIPTION OF THE INVENTION

This invention relates to a method for carrying out a reaction with a catalyst which shows a remarkable temperature rise at the time of reaction due to its large initial activity and in turn the difficulty of control of reaction temperature. More particularly, this invention relates to a method for carrying out a reaction by using such a catalyst as above-mentioned in a plurality of reactors connected in series while properly controlling the activity of the catalyst in each reactor.

When a reaction is carried out by using a catalyst which shows a remarkable rise of reaction temperature due to its large initial activity (so called top-heavy reactivity), there has been heretofore used a method in which a feeding rate of reaction raw materials is reduced for a while during the initial stage of the reaction in order to control side reactions and prevent the damage of a reactor. A method has been also used in which catalyst activity is reduced in advance e.g. by way of a proper catalyst poison. It is, however, evident that the use of such a method is not preferable from catalyst efficiency.

It is an object of the present invention to provide a method for carrying out a reaction with a catalyst which shows a remarkable temperature rise at the time of reaction due to its large initial activity, without injuring the catalyst efficiency and in a practically continuous manner.

The above-mentioned object can be attained by the method completed by us.

We have found that a reaction can be carried out with a catalyst of the above-mentioned kind, practically in a continuous manner, without injuring the catalyst efficiency if a plurality of reactors connected in series and containing a catalyst having different grade of activities by subjecting it to careful initial reaction in each of the reactors are used.

In the method of the present invention, firstly as the catalyst activities in each of the reactors, (a) the first reactor is started with an activity reduced to such an extent as being sufficient to make the control of reaction temperature very easy from the beginning and to reduce notably the feeding amount of unreacted raw materials to the second and the subsequent reactors so as to make the control of reaction temperature in the second and the subsequent reactors also very easy, (b) other reactors are arranged to show activities greater than that of the precedent reactor, respectively and (c) the last reactor is started at a largest extent of activity such that the total conversion attained by all the reactors including other reactors can be maintained at the initial value of total conversion even at a time when the catalyst activity of the first reactor is reduced to unusable extent and thus to be preferable enough, the content of the reaction product can be maintained always uniformly. Secondly, when the catalyst activity of the first reactor is lowered to unusable extent as the result of reaction, the reaction is interrupted, (d) the second reactor is advanced to be used as the first reactor. It is necessary at this time, that the catalyst activity of the second reactor is lowered to such an extent that the second reactor is usable as the first reactor even when it is advanced to the first and this should be controlled in advance (e) each of the reactor in the third and the subsequent order is advanced its order, respectively and (f) the first reactor which has become unusable now, is charged with a catalyst having an activity of the same extent as that of the last reactor in the first run and used circulatory as the last reactor in the next run. Thus after the above-mentioned controlling, the reaction is resumed and the catalytic reaction is carried out by repeating the above-mentioned operation.

Accordingly, by way of the method of the present invention, the feeding rate of the reaction raw material can be maintained at a highest permissible value without lowering, from the beginning and reaction temperature can be controlled easier.

With regard to the reaction in which a catalyst must be exchanged, if it is permissible to provide for a stand-by reactor filled with a new catalyst in advance, considering the time necessary for the exchange of the catalyst and the economy of installation of such a stand-by reactor, it is possible to use such a reactor to make the time of interruption of a reaction as short as possible. Further if no obstacle occurs even by using only the reactors other than the reactor in which a catalyst must be exchanged during the time of exchange of the catalyst, it is possible to use such a process provisionally.

Following examples are provided to illustrate the present invention but it is not intended to limit the invention.

EXAMPLE

Description will be made in a case of preparation of cyclohexane by way of hydrogenation of benzene using two multitubular reactors.

In the inside of the tubes of a multitubular reactor, a catalyst consisting of, as principal components, nickel and nickel oxide and as a carrier, diatomaceous earth were charged and a provision was made so as to generate low pressure steam from the outside of the tubes (i.e. shell side) to control reaction temperature.

In the first reactor, a catalyst which had been treated in advance with the amount of the benzene corresponding to a quarter of the total amount of the benzene which had been assumed to be treated with a new catalyst alone, while paying the attention to the initial activity, was employed.

In the second reactor which was of the same type with the first reactor, a new catalyst was charged. The reaction was carried out with the above-mentioned arrangement of the reactors by using a raw material benzene having a purity of 99.97% or more and 1.8 times the theoretical amount of hydrogen, by circulating unreacted material consisting mainly of hydrogen for reuse and under the conditions of a temperature of about 160° C and a pressure of about 20 Kg/cm² gauge whereby the raw material could be fed in an allowable maximum amount from the beginning and cyclohexane having a purity of 99.96% or more could be obtained. When the first reactor was used until the catalyst activity was almost exhausted, the capacity of the catalyst of the second reactor was lowered to about a quarter of the initial capacity. Thus the reaction was interrupted at this monment and the second reactor was used as the first reactor in the next run and the reactor which had been used as the first reactor in the first run, was charged with a new catalyst to be used as the second reactor in the second run. Thus the same result was obtained in the second run as in the first run by using the same operational conditions.

Further the activity of the catalyst in the upper layer in the tubes of the first reactor was reduced and this part seems to catch the catalyst poison such as thiophenes or accompanying heavier oil, resulting in the concomitant preferable influence upon the catalyst life.

What is claimed is:

1. In the known process for producing cyclohexane by the hydrogenation of benzene in the presence of a catalyst consisting of nickel and nickel oxide supported on diatomaceous earth under hydrogenation conditions, the improvement which comprises
   (1) providing two separate multitubular catalytic reaction zones,
   (2) filling the first of said catalytic reaction zones with a catalyst having an activity reduced by the treatment of the amount of benzene corresponding to about one-fourth of the amount of benzene treatment,
   (3) filling the second of said catalytic reaction zones with a catalyst having a high activity and which has not been subject to the treatment set forth in (2),
   (4) passing benzene sequentially through said first catalytic reaction zone and then thru said second catalytic reaction zone until the catalytic activity in said first catalytic reaction zone is reduced to almost zero,
   (5) replacing the spent catalyst in said first catalytic reaction zone with highly active catalyst,
   (6) passing benzene to be hydrogenated through said second catalytic reaction zone and then through said first catalytic reaction zone until the catalytic activity in said second catalytic reaction zone is reduced to almost zero,
   (7) replacing the spent catalyst in said second catalytic reaction zone with highly active catalyst, and
   (8) repeating the above sequence of catalyst replacement steps and benzene flow any desired number of times.

* * * * *